United States Patent [19]
Tanner et al.

[11] Patent Number: 5,972,023
[45] Date of Patent: Oct. 26, 1999

[54] IMPLANTATION DEVICE FOR AN AORTIC GRAFT METHOD OF TREATING AORTIC ANEURYSM

[75] Inventors: Howard Miles Tanner, Salt Lake City, Utah; Hugh Henry Trout, III, Washington, D.C.

[73] Assignee: Eva Corporation, Bethesda, Md.

[21] Appl. No.: 08/692,127

[22] Filed: Aug. 5, 1996

Related U.S. Application Data

[63] Continuation of application No. 08/290,124, Aug. 15, 1994, abandoned.

[51] Int. Cl.$^6$ .................................................. A61B 17/04
[52] U.S. Cl. ........................... 606/219; 606/153; 623/12; 227/19
[58] Field of Search ................................. 606/213, 219, 606/153; 623/12; 227/19, 175, 178, 179

[56] References Cited

U.S. PATENT DOCUMENTS

| | | | |
|---|---|---|---|
| 4,562,596 | 1/1986 | Kornberg | 623/1 |
| 4,787,899 | 11/1988 | Lazarus | 623/1 |
| 5,042,707 | 8/1991 | Taheri | 606/213 |
| 5,207,695 | 5/1993 | Trout, III | 606/153 |

Primary Examiner—Gary Jackson
Attorney, Agent, or Firm—Collier, Shannon, Rill & Scott, PLLC

[57] ABSTRACT

A surgical stapler and method for implanting an aortic graft with staples to treat an aortic aneurysm. A prosthetic graft is implanted within the aorta to functionally replace the segment of the aorta damaged by an aneurysm. The stapler would typically be used where the graft is to be attached to an area of the aorta which lacks sufficient healthy tissue to ensure secure attachment by conventional fasteners such as when an aneurysm develops near the iliac arteries. The graft is implanted with staples fired from the surgical stapler. The stapler consists of a stapling device attached to the end of a modified catheter by a hinge. In order to allow greater flexibility in positioning the staples, a mechanism may be used to move the stapling device into the desired angle or position to implant the staple. The stapler may be positioned and fired by remote control. The staples consist of a base member, posts located at both ends of the base member and radiating away from the base member, and a hook attached to the distal end of each shank. The hook may also consist of several barbs. The barbs may be orientated inward to minimize injury to surrounding tissue.

28 Claims, 13 Drawing Sheets

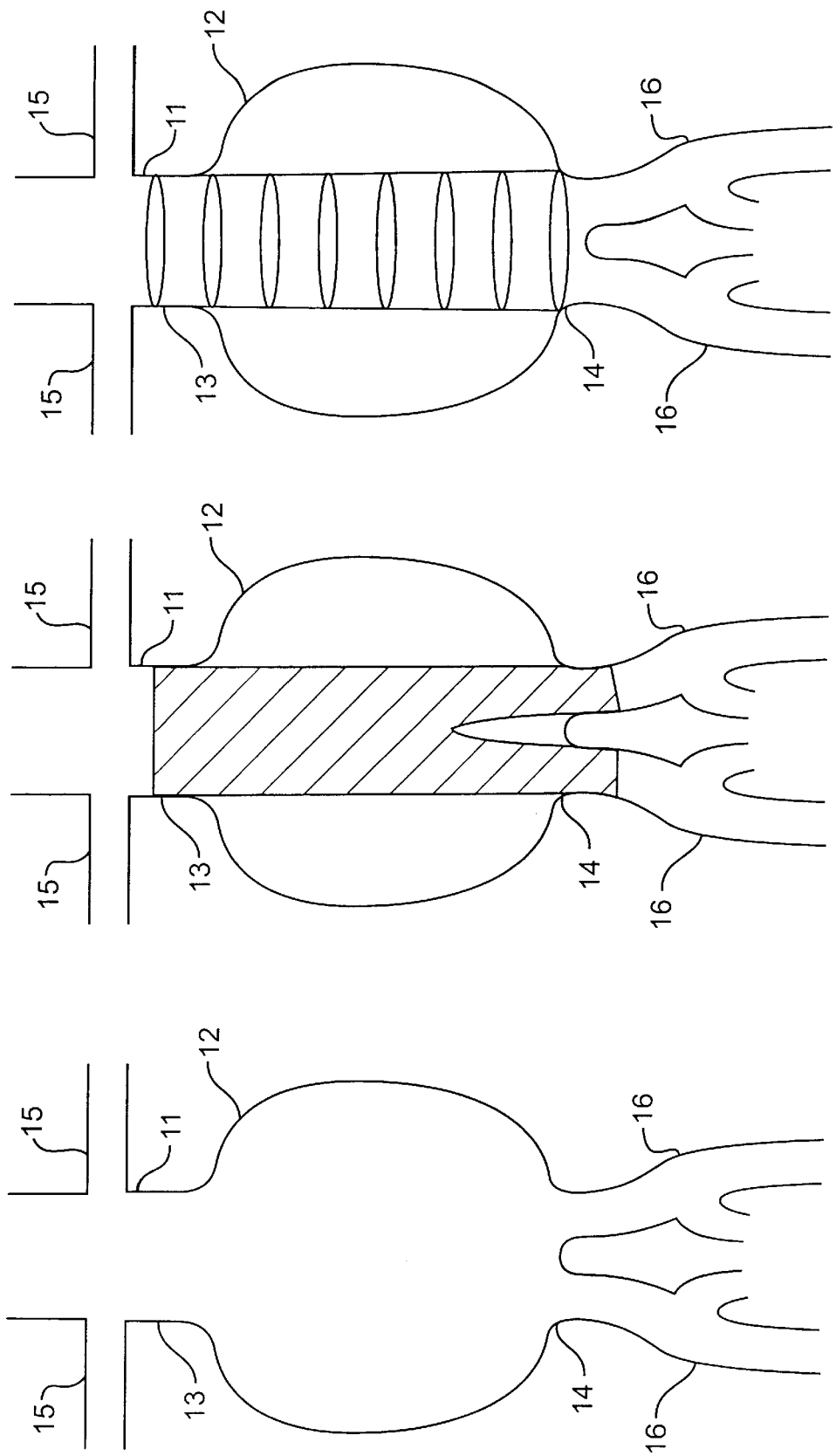

IMPLANTATION DEVICE FOR AN AORTIC GRAFT METHOD OF TREATING AORTIC ANEURYSM

RELATED APPLICATIONS

This application is a continuation of U.S. patent application Ser. No. 08/290,124 filed Aug. 15, 1994 now abandoned.

The invention is an implantation device and method of using same to implant an aortic graft to repair and treat aortic aneurysms. The present invention is an improvement on the system previously patented by Trout, U.S. Pat. No. 5,207,695, for Aortic Graft, implantation Device, and Method for repairing aortic aneurysm, which is incorporated herein by reference. The present invention, however, is not limited to use with Trout's prior invention and it will be apparent to those skilled in the art that the present invention is unique and has additional applications.

An aneurysm is a ballooning of the wall of an artery resulting from the weakening of the artery due to disease or other conditions. Left untreated, the aneurysm will frequently rupture, resulting in loss of blood through the rupture.

Aortic aneurysms are the most common form of arterial aneurysm and are life threatening. The aorta is the main artery which supplies blood to the circulatory system. The aorta arises from the left ventricle of the heart, passes upward and bends over behind the heart, and passes down through the thorax and abdomen. Among other arterial vessels branching off of the aorta along its path, the abdominal aorta supplies two side vessels to the kidneys, the renal arteries. Below the level of the renal arteries, the abdominal aorta continues to about the level of the fourth lumbar vertebrae (or the navel), where it divides into the iliac arteries. The iliac arteries, in turn, supply blood to the lower extremities and perineal region.

It is common for an aortic aneurysm to occur in that portion of the abdominal aorta between the renal arteries and the iliac arteries. This portion of the abdominal aorta is particularly susceptible to weakening, resulting in an aortic aneurysm. Such an aneurysm is often located near the iliac arteries. An aortic aneurysm larger than about 4 cm in diameter in this section of the aorta is ominous. Left untreated, the aneurysm may rupture, resulting in rapid, and usually fatal, hemorrhaging.

Aneurysms in the abdominal aorta are associated with a particularly high mortality rate. Accordingly, current medical standards call for urgent operative repair of abdominal aortic aneurysms. Abdominal surgery, however, results in substantial stress to the body. Although the mortality rate for an aortic aneurysm is extremely high, there is also considerable mortality and morbidity associated with surgical intervention to repair an aortic aneurysm. This intervention involves going through the abdominal wall to the location of the aneurysm to bypass or replace the diseased section of the aorta at the aneurysm. A prosthetic device, typically a synthetic tube, is used for this purpose. The graft serves to exclude the aneurysm from the circulatory system, thus relieving pressure and stress on the weakened section of the aorta at the aneurysm.

Repair of an aortic aneurysm by surgical means is a major operative procedure. Substantial morbidity accompanies the procedure, resulting in a protracted recovery period. Further, the procedure entails a substantial risk of mortality. While surgical intervention is, nonetheless, called for in the case of an aortic aneurysm in spite of these risks, certain patients may not be able to tolerate the stress of intra-abdominal surgery. It is, therefore, desirable to reduce the mortality and morbidity associated with intra-abdominal surgical intervention.

In recent years, methods have been developed to attempt to treat an aortic aneurysm without the attendant risks of intra-abdominal surgical intervention. Among them are inventions disclosed and claimed in Kornberg, U.S. Pat. No. 4,562,596 (Jan. 7, 1986) for Aortic Graft, Device and Method for Performing an Intraluminal Abdominal Aortic Aneurysm Repair; Lazarus, U.S. Pat. No. 4,787,899 (Nov. 29, 1988) for Intraluminal Graft Device, System and Method; and Taheri, U.S. Pat. No. 5,042,707 for Intravascular Stapler, and Method of Operating Same.

Kornberg discloses an aortic graft comprising a flexible tubular material having a plurality of struts to lend the graft stability and resiliency. The struts have angled hooks with barbs at their upper ends which are securely attached to the inside of the aorta above the aneurysm. Kornberg's graft is inserted using a tubular device also disclosed in his patent. Kornberg, however, anchors the graft at only the proximal end of the graft. Kornberg claims that the downward flow of blood holds the distal graft securely in place, so that no mechanical attachment is necessary distally. Kornberg, U.S. Pat. No. 4,562,596, Col. 6, lines 24–27. The blood pressure in the abdominal aorta, however, is typically in the magnitude of 130 mm of mercury. In spite of the direction of flow of blood through the graft, proximal to distal, substantial back pressures within the aneurysm will result unless the distal end is also mechanically attached to the aorta in a manner that prevents substantial leakage of blood between the graft and the aorta. Without distal attachment, the device of Kornberg will not effectively exclude the weakened arterial wall at the site of the aneurysm from the forces and stress associated with the blood pressure.

Lazarus discloses a grafting system that employs a plurality of staples mounted in the proximal end of the graft. Lazarus's staples are forced through the aorta wall by means of a balloon catheter. As does Kornberg, Lazarus discloses staples mounted only in the proximal end of the graft. There is no teaching or suggestion in Lazarus, U.S. Pat. No. 4,787,899 as to the desirability of, let alone means for mechanically attaching the graft to the distal aorta below the level of the aneurysm.

Taheri discloses an articulatable stapler for implanting a graft in a blood vessel. The stapler is in the form of an elongated catheter with a plurality of segments mounted on the distal end of the catheter. The segments have beveled faces and are connected to each other by hinges. A stylet runs through the catheter to the most distal segment. The most distal segment is moved, in conjunction with the other segments, into a firing position that is substantially perpendicular to the main catheter body by the action of pulling on the stylet. The staple is implanted by using two other stylets which act as fingers to bend the staple into its attachment position.

Taheri, however, appears to be a single-fire design which can only implant one staple at a time. After each stapler is implanted, Taheri's design apparently requires that the catheter be removed before another staple is loaded. In addition, Taheri's does not teach or suggest an appropriate density of staples to secure a graft against the pulsatile blood flow of the aorta. Pressures within the aorta range from 120 mm Hg pressure to 200 mm Hg pressure. Without adequate attachment, the graft may leak around the edges continuing to allow life threatening pressures to develop in the aneurysm, and may not even remain in place.

Hence, although in recent years certain techniques have been developed that may reduce the stress, morbidity, and risk of mortality associated with surgical intervention to repair aortic aneurysms, none of the systems that have been developed effectively treat the aneurysm and exclude the affected section of aorta from the pressures and stresses associated with circulation. None of the devices disclosed in the references provide a reliable and quick means to bypass an aneurysmal artery. In addition, all of the prior references require a sufficiently large section of healthy aorta surrounding the aneurysm to ensure attachment of the graft. The neck of the aorta at the cephalic end above the aneurysm is usually sufficient to maintain a graft's attachment means. However, when an aneurysm is located near the iliac arteries, the aorta below the aneurysm may form a broad and distended neck. Such an ill-defined neck would have an insufficient amount of healthy aortic tissue to hold securely any conventional attachment at the caudal end of the graft.

A recent patent to one of the present inventors, Trout, U.S. Pat. No. 5,207,695 for Aortic Graft, Implantation Device, and Method for Repairing Aneurysm (May 4, 1993), overcomes many, but not all, of these challenges. In particular, Trout discloses a balloon catheter implantation device. In areas where the artery wall is heavily calcified, implantation by balloon catheter may be difficult or impossible.

It is therefore an object of the invention to provide a method to repair an aortic aneurysm with a much lower risk of morbidity and mortality than that associated with surgical procedure for the repair of the aneurysm.

A further object of the invention is to provide an improved surgical stapler for securely implanting an aortic graft.

A further object of the invention is to provide a method to aid the replacement of an aneurysm of the abdominal aorta by assisting the positioning and fixation of a prosthetic graft within the distal aorta.

A further object of the invention is to provide an improved implantation device that is adapted to be inserted longitudinally into an aorta securely implanting an aortic graft to the interior surface of the aorta.

A further object of the invention is to provide an improved implantation device, with a distal portion which may be moved in a variety of positions relative to the main stapler body.

A further object of the invention is to provide an improved staple design for securely attaching a graft to an aorta.

A further object of the invention is to provide a method of introducing the improved surgical stapler into the surgical site through the femoral of iliac arteries while its use is being controlled externally to the body.

A further object of the invention is to provide an improved positioning device design for securely positioning the surgical stapler for attaching a graft to an aorta.

A further object of the invention is to provide an improved control device for controlling the functioning of the surgical stapler and positioning device for securely positioning the surgical stapler and for attaching a graft to an aorta.

A further object of the invention is to provide an improved visualization device for controlling the functioning of the surgical stapler and positioning device for securely positioning the surgical stapler and for attaching a graft to an aorta.

A further object of the invention is to provide an improved means for attachment of a graft to a vessel.

SUMMARY OF THE INVENTION

As illustrated in the accompanying drawings and disclosed in the accompanying claims, the invention is an implantation device for implanting a substantially cylindrical aortic graft means, having cephalic and caudal ends, comprising a device having a distal end adapted to be introduced into an animal for attaching a repair member to an animal vessel, and a proximal end external of the animal, said device comprising at the distal end, means for storing plural attachment members adapted to attach the repair member to the vessel; and means for inserting one of said attachment members at a time through the repair member and the vessel to thereby connect the repair member and the vessel; and comprising at the proximal end, means for controlling the operation of said means for storing and means for inserting such that said means for storing delivers one attachment member at a time to said means for inserting and said means for inserting applies pressure to said attachment member to insert the attachment member in through the repair member and the vessel.

BRIEF DESCRIPTION OF THE DRAWINGS

The characteristics and features of the present invention will be better understood through the following detailed description and accompanying drawings which are incorporated herein by reference. It is to be understood that both the foregoing general description and the following detailed description are exemplary and explanatory only, and are not restrictive of the invention as claimed. The accompanying drawings, which are incorporated herein by reference, and constitute a part of the specification, illustrate certain embodiments of the invention, and together with the detailed description, serve to explain the principles of the present invention.

FIG. 4 is, and in particular

FIG. 8 is, and in particular FIGS. 8A, 8B, and 8C are, a series of coronal views of an aortic aneurysm. In FIG. 8A, the distal end of the aneurysm extends to such close proximity to the iliac arteries that no neck remains for the attachment of the distal end of the graft by prior methods. FIG. 8B is a coronal view of a bifurcated graft implanted in the aneurysm. FIG. 8C is a coronal view of the aneurysm and graft, showing that where the distal end of the aneurysm extends in such close proximity to the iliac arteries, implantation of tubular grafts is complicated by the lack of a caudal neck in the aorta.

DESCRIPTION OF A PREFERRED EMBODIMENT

Figure 1:
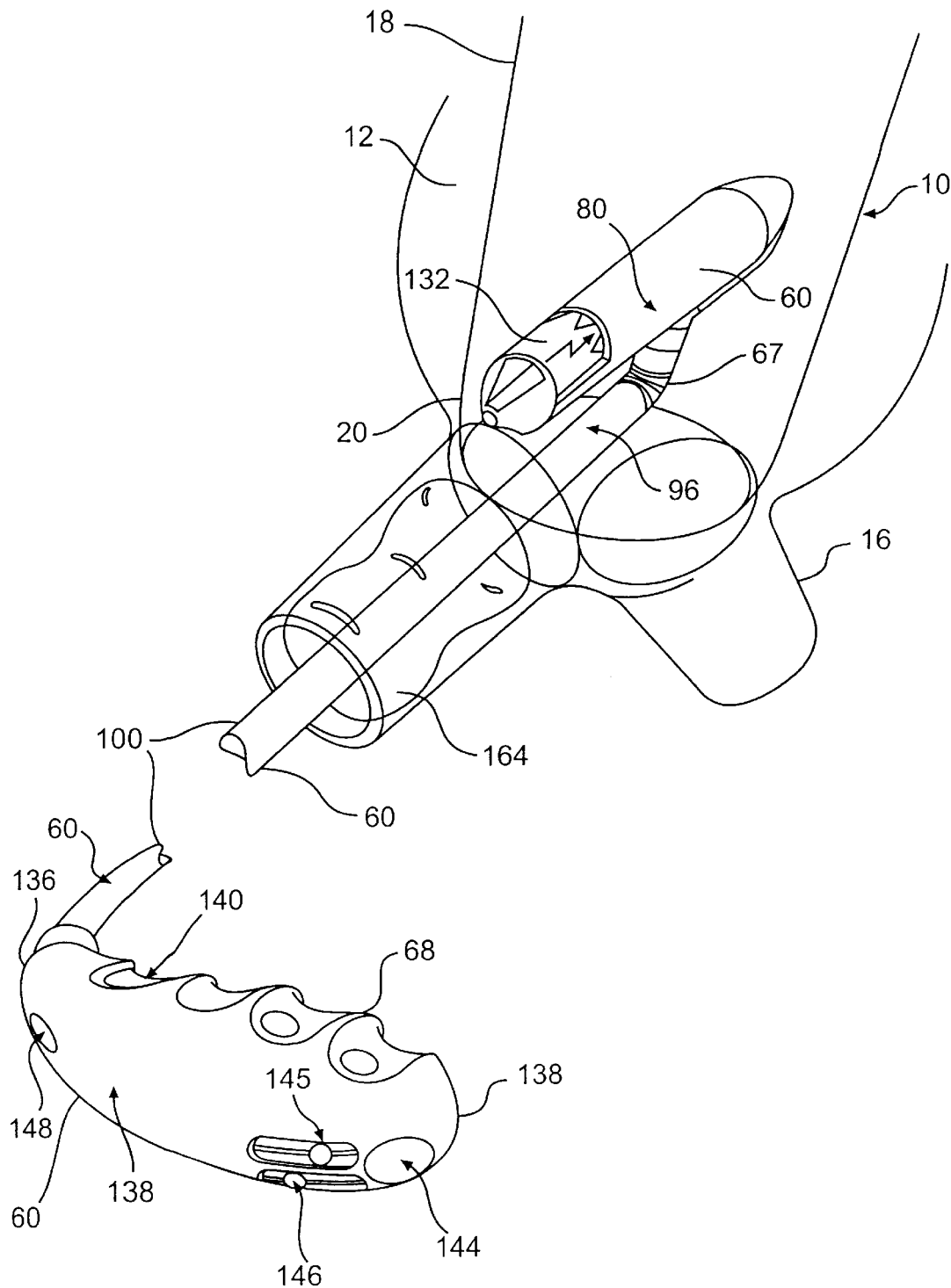
FIG. 1 is an enlarged oblique view of the implanting means and the distal end of the positioning means of one embodiment of the implanting device of the present invention.
Figure 6B:
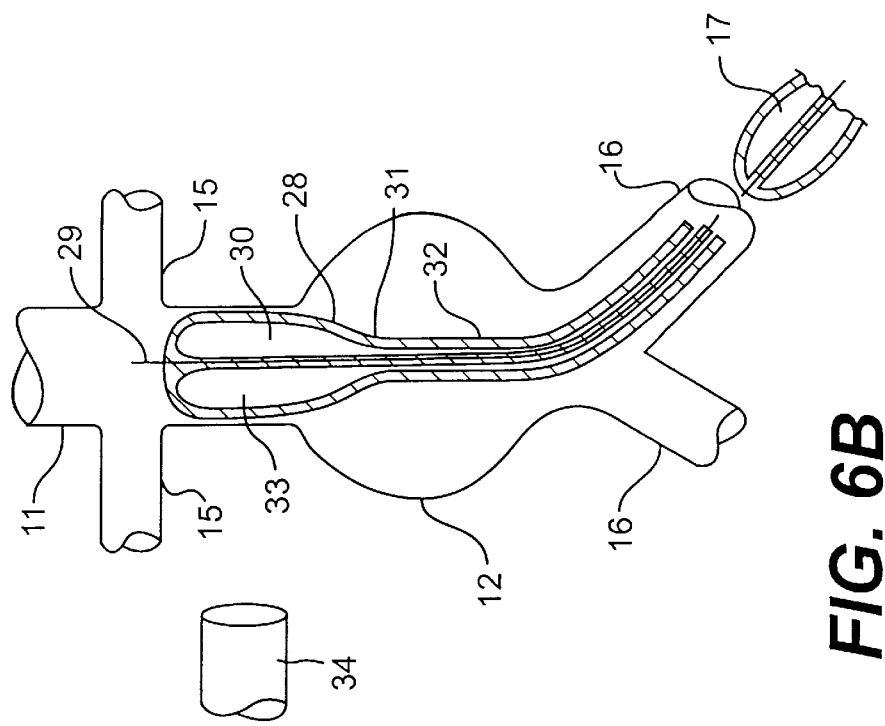
FIG. 6B is a coronal view of a balloon catheter being inserted into the cephalic end of the affected artery above the aneurysm in order to measure the diameter of the vessel.
Figure 6A:
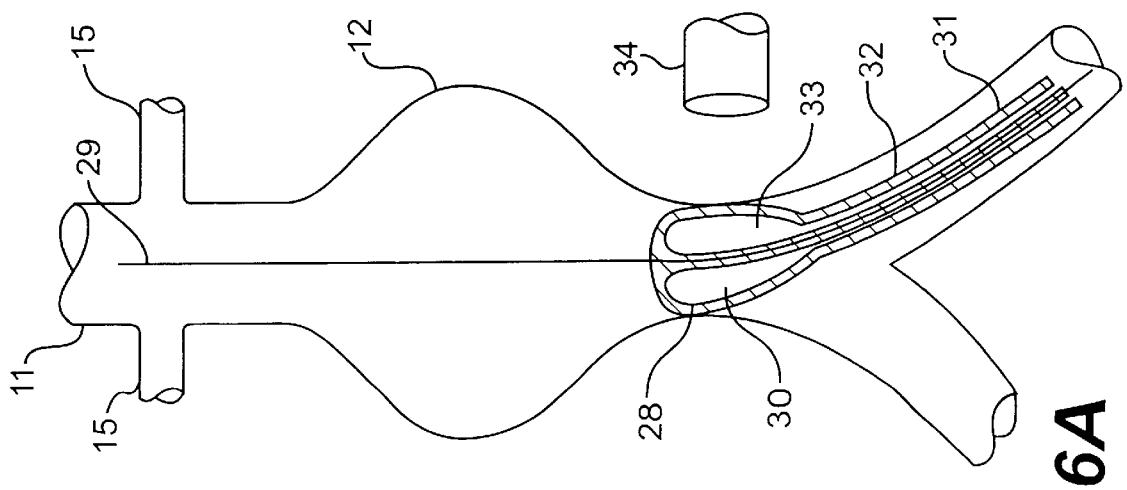
FIG. 6A is a coronal view of a contrast filled balloon catheter being inserted into the caudal end of the abdominal artery below the aneurysm to measure the diameter of the vessel.

FIG. 1 illustrates a preferred embodiment of implantation device 60 of the present invention. Implantation device 60 is used to implant aortic graft means 10 for repairing an abdominal aortic aneurysm 12. As illustrated in FIG. 6, the aortic aneurysm 12 is located in the abdominal aorta 11 between the renal arteries 15 and the iliac arteries 16.

It will be apparent to those skilled in the art that an aortic graft 10 and the implanting device 60 of the present invention can also be used in other applications without departing from the scope or spirit of the appended claims. For example, the graft could be used on any type of fluid conducting vessel such as sections of arteries located in other parts of the body or other types of vessels.

Implantation device 60 of the present invention comprises: positioning means 96; attachment means 22; implanting means 80; and control means 136. Implantation device 60 is used in conjunction with a guide wire 29 and occlusal balloon 170 to implant an aortic graft 10 in an aneurysm 11, thereby excluding the aneurysm from the forces of blood pressure, as a therapy for the treatment and management of aortic aneurysm.

Figure 7B:
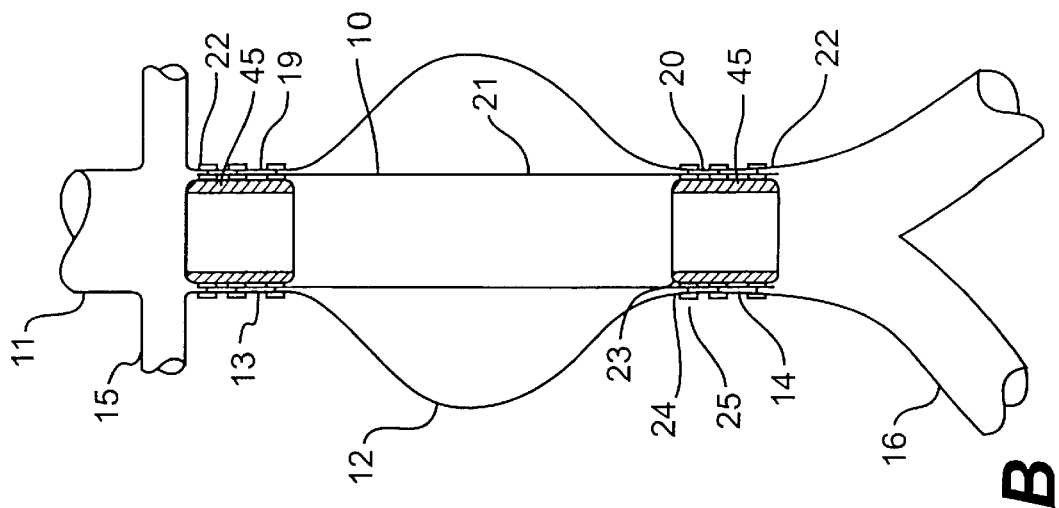
FIG. 7B is a coronal view of an aortic graft of Trout, U.S. Pat. No. 5,207,695, after attachment means of cephalic and caudal ends have been implanted in the aorta wall, stents have been implanted, and the double balloon catheter system has been withdrawn, excluding the aneurysm.
Figure 7A:
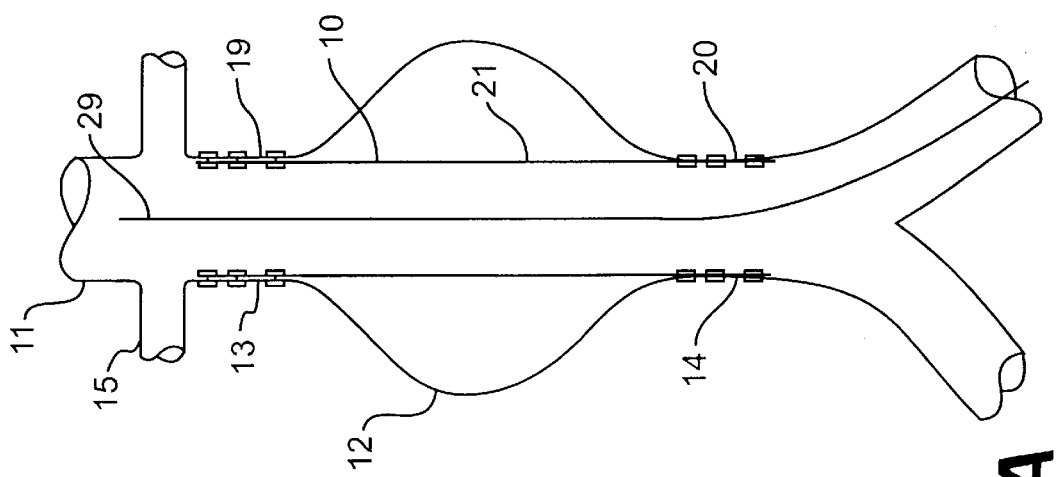
FIG. 7A is a coronal view of an aortic graft of Trout, U.S. Pat. No. 5,207,695, after attachment means of cephalic and caudal ends have been implanted in the aorta wall and the double balloon catheter system has been withdrawn, excluding the aneurysm.

As shown in FIGS. 7A and 7B aortic graft 10 has cephalic 19 and caudal 20 ends and a body 21. Aortic graft 10 is preferably fabricated from a flexible, yet resilient, material such as polytetrafluoroethylene (Teflon) or other material having similar flexible and resilient properties. Other substance such as natural or synthetic polymeric substances (such as polyester fabric, Dacron, Mylar, Rayon, cellulose acetate, cellulose butynate) may also be used. A critical consideration is that the substance of which the aortic graft 10 is made be biologically inert and be compatible with the tissues into which the aortic graft is to be implanted. Many materials of this type are well known in the art.

Consistent with the present invention, the cephalic or proximal end 19 of the aortic graft 10 may be attached to the aorta above the aneurysm 12 by any suitable attachment means 22. In a preferred embodiment of the present invention, attachment means 22 of the present invention is one of the various types of surgical staple depicted in the appended drawings, and in particular, of the type shown in FIG. 4D.

As shown in FIGS. 7A and 7B, cephalic attachment means 22 can also comprise the attachment means of Trout '695, or of the present invention, or any other appropriate attachment means, capable of providing secure attachment. For example, the attachment means disclosed and claimed in Trout '695 patent comprise base means 23, post means 24, and hook means 25. Hook means 25, may in turn, further comprises a tip 26 to facilitate penetration of aorta 11 by the hook means 25 and a barb to resiliently hold attachment means in an implanted position relative to the aorta 11. In a preferred embodiment of the present invention, the aortic graft 10, is provided with a plurality of attachment means 22, mounted in the cephalic 19 end of aortic graft 10. Absent the types of medical indications that are discussed in this application, cephalic attachment means of the graft 10 is preferably that disclosed and claimed in Trout '695, by virtue of its ease on implantation.

In many patients, however, the attachment means disclosed and claimed in Trout '695 and in other prior graft attachment devices are either not appropriate or effective or are contraindicated for various other reasons. In these situations, attachment means 22 of the present shown in FIGS. 4A–4G, inclusive, may be preferred. This will typically occur at the caudal end of the aneurysm but may occur at the cephalic end of the aneurysm as well. For example, with renewed reference to FIGS. 7A and 7B, the caudal end of the aneurysm, in a majority of patients who present with abdominal aortic aneurysm, provides insufficient aortic neck for the attachment of the distal end of the graft 10 by prior known means. In addition, the interior of the artery wall may be calcified. Calcification will resist, or may even prevent, the implantation of the graft 10 by prior methods, including those disclosed in Trout '695. In these cases, the present invention provides a means to implant the graft. Where the present invention is used to implant the graft at the caudal end 20 of the graft, it will often be more convenient and faster, and therefore, more appropriate as a matter of good surgical procedure, to use the implantation means of the present invention at the cephalic end 19 as well.

Figure 2A:
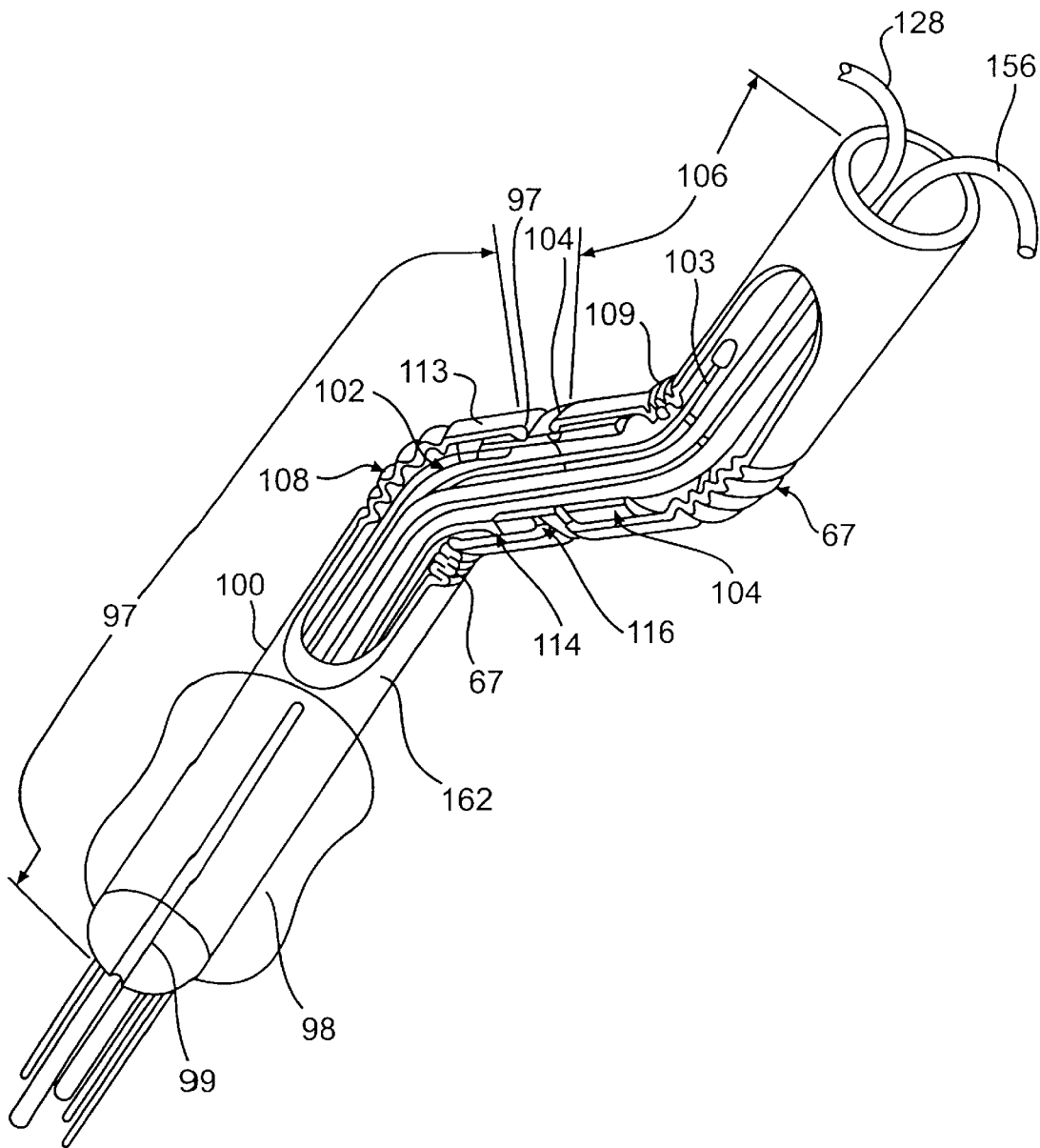
FIG. 2A is a partial cut-away, oblique view of a portion of the distal end of the positioning means of the present invention.

The following is a general description of the operation of the claimed invention, followed by a more detailed description of the present preferred embodiment. Implantation device 60 is shown in FIG. 1, as comprising implanting means, such as for example a stapler 80 attached to the distal end of a modified catheter with an actuating means (positioning means 96), and controls 136. With reference to FIG. 2A the actuating means 108 and 109 allow the stapler 80 to be easily manipulated into optimal firing positions to fire staples 132 through the graft 10 and into the aorta wall. The staples 132 may comprise base means 73, post means 74, and barb means 77, as shown in FIG. 4D, to resiliently hold attachment means in an implanted position relative to the aorta 11.

With reference to FIGS. 4A, 4B, 4E and 4G, base means 73, is constructed of a biologically compatible material such as metal or plastic. For example, base 73 can be a flat strip of metal of approximately 3 to 4 mm in length. Post means 74 is a post that is preferably oriented in substantially perpendicular relation to base 73. Post 74 can be mounted on both ends of base 73 so that post 74 extends radially outward from the axis of aortic graft 10 when base 73 is mounted in relation to aortic graft 10. Each post means 74 is preferably approximately 4 mm long. Base 73 may be secured to the post 74 through a variety of means including gluing, riveting, welding, or other means that are biologically compatible and will provide a secure attachment of post 74 to base 73. In the lumen of aortic graft 10, the distal surface of base 73 will abut the proximal surface of the lumen of aortic graft 10 so that post 74 penetrates and extends through aortic graft 10.

Figure 4A:
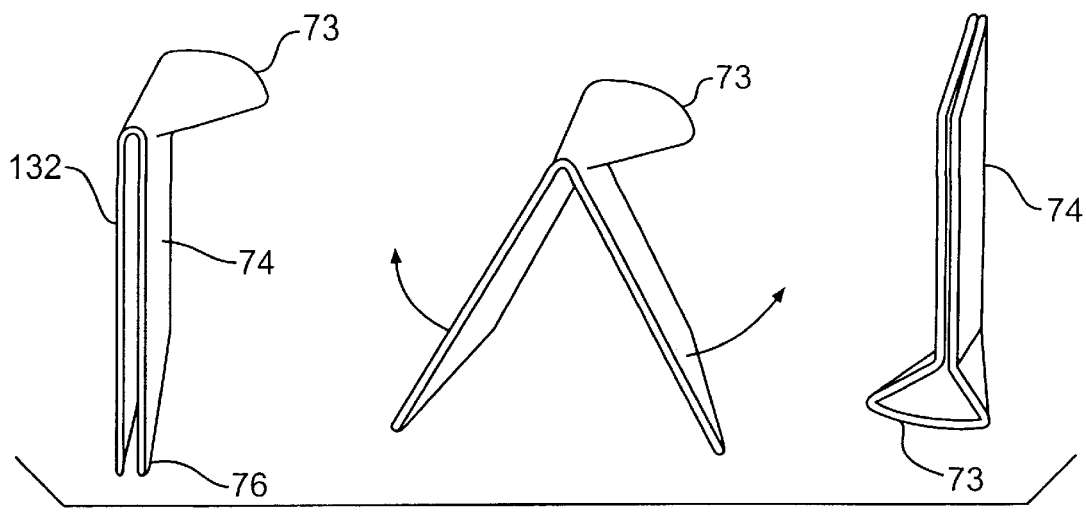
FIGS. 4A through 4G are, a series of oblique views of certain variations and modifications of embodiments of the attachment means of the present invention.
Figure 4B:
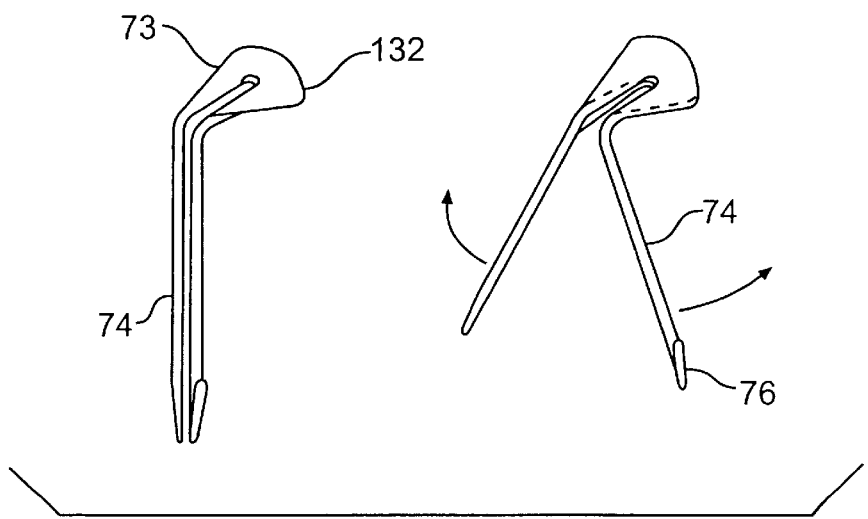
Figure 4C:
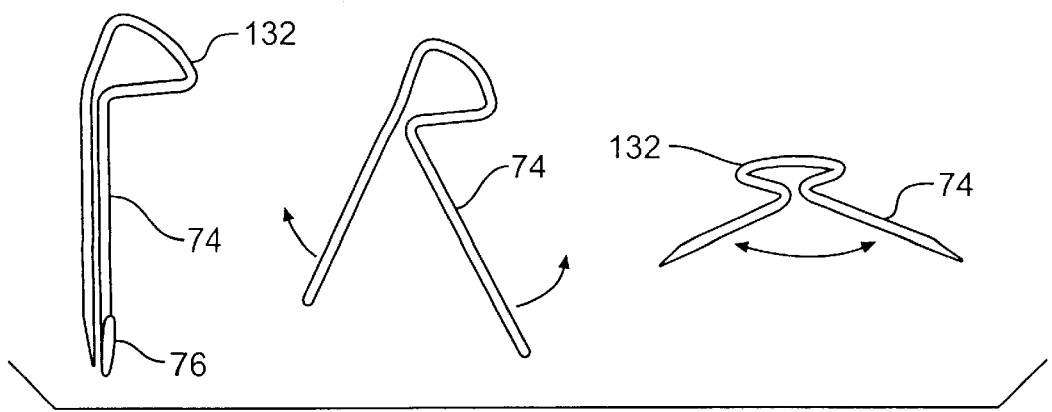
Figure 4D:
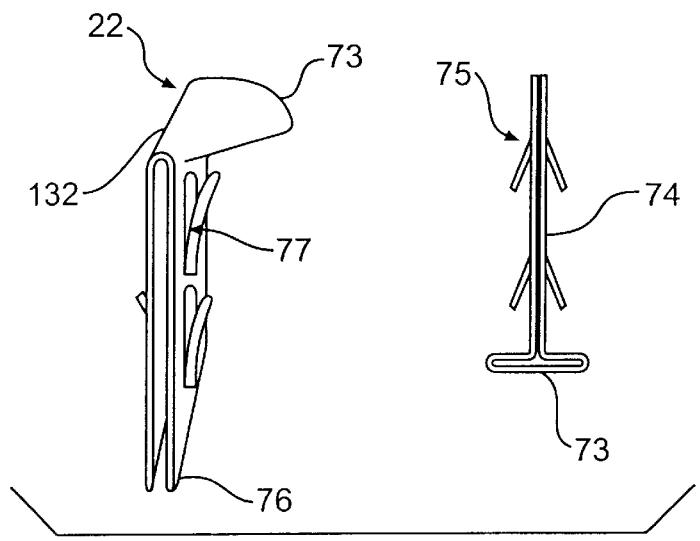
Figure 5:
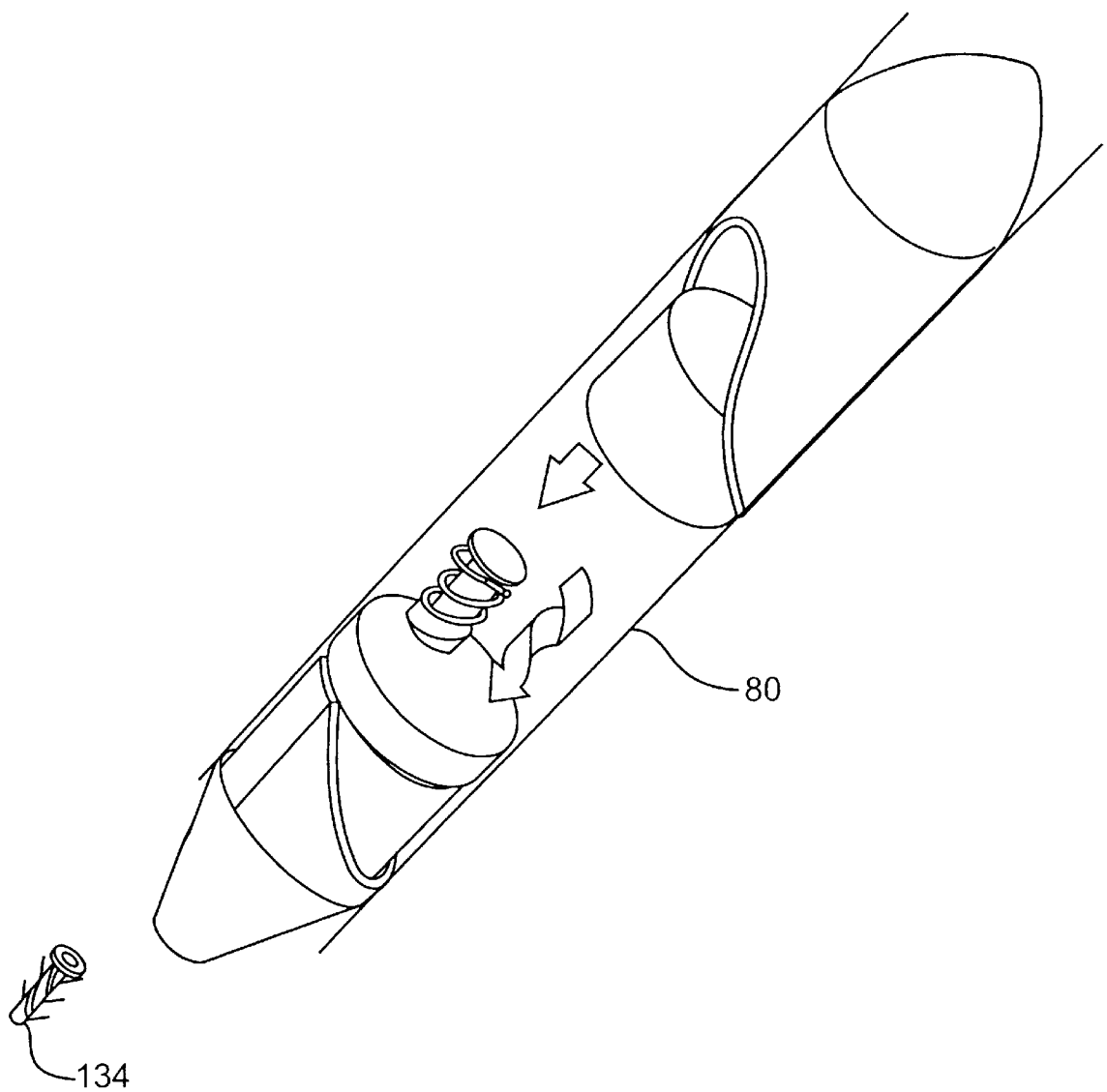
FIG. 5 is a cut-away, partial, side exploded view of one alternative preferred embodiment of the implantation means and attachment means of the present invention in which the implantation means is adapted to penetrate calcified areas of the aorta wall that may resist or impede the penetration of alternative attachment means such as those shown in FIG. 4.

With reference to FIG. 4D, hook means 75 is preferably mounted on the distal end of a post 74. Further, hook means 75 may consist of one or more barbs 77 for holding the aortic graft 10 firmly in place relative to the aorta 11, as shown in FIGS. 4D and 5. Barbs 77 are approximately 1 mm long, and should be spaced about 1 to 1.3 mm apart from one another. Preferably, there should be a maximum of three barbs on each post 74, for a maximum of six barbs on each staple means 132.

Figure 2B:
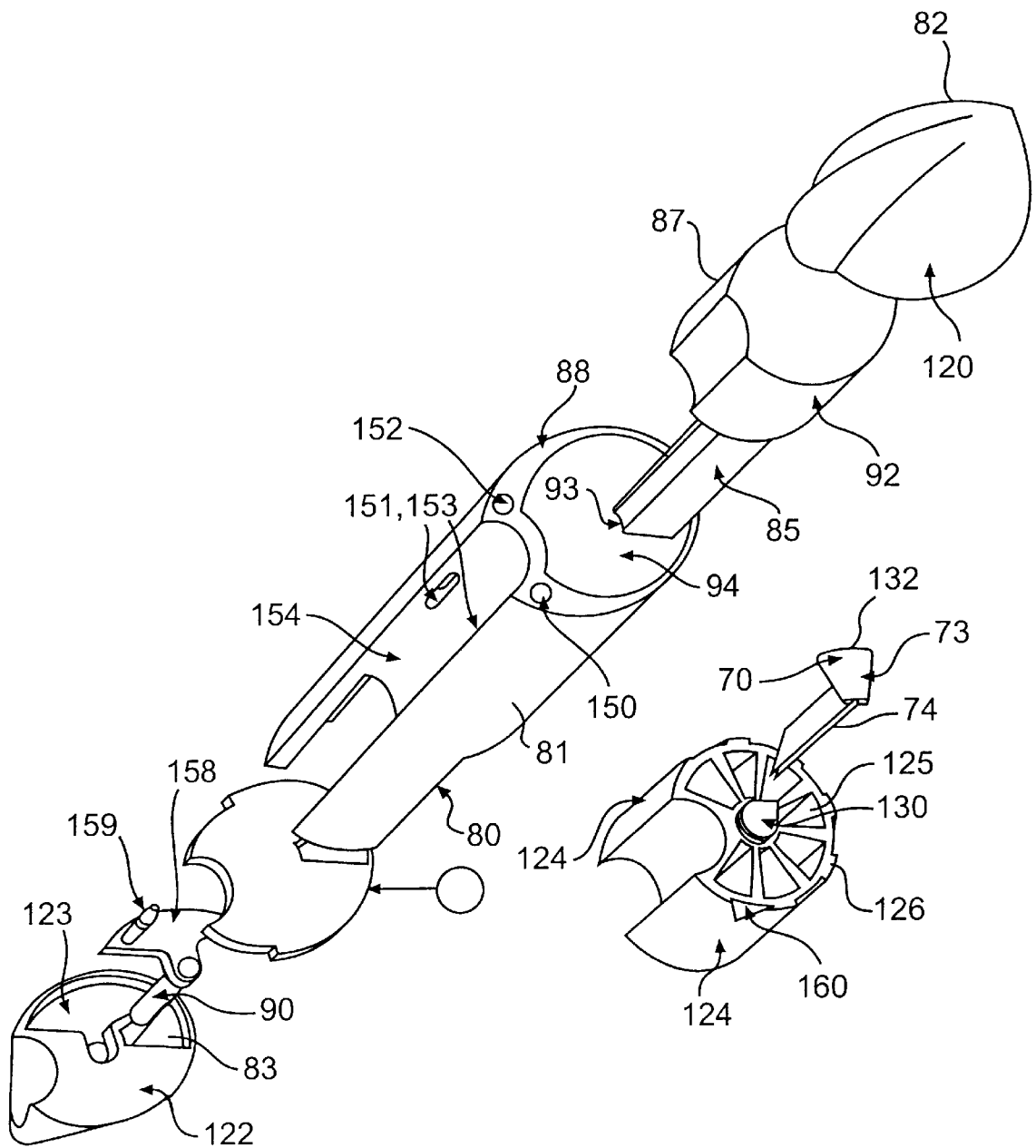
FIG. 2B is a partial cut-away, oblique view of one embodiment of the positioning means of the present invention.

With reference to FIG. 2B, the length of stapler 80 is preferably less than two (2) inches. Alternatively, the length of stapler 80 depends on the degree to which it is required to rotate in the radial direction of the vessel. In the event it is desired that the stapler 80 be longer, it can be angled into an "L-shaped" configuration to allow space for the desired components while still fitting within the vessels. Stapler 80 contains a magazine 124 staples 132. Staples 132 are ejected straight out of the of the stapler 80 through slot 83. The staple 132 is primed and positioned over desired spot. Piston 92 may apply pressure to the base 73 of staple 132 when it is in position, and implants staple 132 into the graft 10 and the aorta wall. Piston 92 may be activated by remote control 136. Force is developed by Driver through bursts of compressed air.

As noted above, implantation device 60 of the present invention comprises: positioning means 96; attachment means 22; implanting means 80; and control means 136. In a present preferred embodiment of the invention, implantation device 60 is a surgical stapler, adapted for be percutaneous use, for endovascular insertion of a graft 10. The invention is adapted to achieve secure long-term attachment of the graft 10, to exclude the aneurysm tissue from arterial pressure, and to reduce complications relative to prior methods or aneurysm repair. Being adapted for percutaneous use, the inventors believe that the present invention will achieve same day, "in and out" aneurysm repair, with fewer complications than encountered with prior methods.

With reference to FIG. 2B, implanting means 80 comprises a stapler means 81 and visualization means 90. More specifically, the implanting means comprises a stapler barrel 88; a barrel cap 120; a barrel tip 122; a visualization means 90; an attachment means cartridge 124; an attachment means reservoir 125; and a piston means 92.

Stapler barrel 88 of the present invention is preferably injection molded of liquid crystal, such as that provided by RTP Co. of Minnesota. Alternatively, stapler barrel 88 can be injection molded of similar polymer or extruded of aluminum or stainless steel. The barrel portion is substantially elliptical in profile and preferably has several lumens formed therein: a first, large, substantially circular lumen 94, in which piston 92 moves; a second smaller lumen 150, substantially circular in shape, communicating with positioning means 96 and control means 136, through which compressed air travels to actuate piston 92; and a third small lumen 152, also substantially circular in shape, through which signal and power lines for visualization means 90 (preferably an ultrasound probe) are placed. The outer surface of stapler barrel 88 has an outward facing circular concavity 154 formed therein, into which the proximal positioning tube 106 is permanently attached, as shown in FIGS. 2A and 2B. Apertures 151 and 153 are formed therein to allow the passage of compressed air and power/signal lines.

In a preferred embodiment of the present invention, implanting means 80 also comprises a barrel cap 120 and barrel tip 122. Barrel cap 120 is preferably injection molded of liquid crystal or similar polymer and is bonded via a stepped shoulder detail to the distal end of stapler barrel 88. Barrel cap 120 is preferably detailed to facilitate the communication of compressed air between supply line 156 of positioning means 96 and the upper end of first lumen 94, containing piston 92.

Barrel tip 122 is also preferably molded of liquid crystal or similar polymer. Barrel tip 122 is preferably bonded, via a stepped shoulder to the proximal end of stapler barrel 88. Barrel tip 122 is preferably detailed to accept, visualization means (ultrasound probe) 90 and, staple cartridge 124.

In a present preferred embodiment of the invention, an EndoSonics ultrasound probe 90, mounted on circuit board 158 is disposed in a pocket 123 formed in barrel tip 122. Power and information lines 128, preferably in flexible membrane form, pass through third lumen 98 of stapler barrel 88 and connect via a plug 159 into printed circuit board 158.

In the preferred embodiment of the present invention, staple cartridge 124, molded of high density polyethylene, or similar polymer, is detailed to be detachably assembled into stapler barrel 88 assembly. Attachment means (stapler) cartridge 124 contains a "procedure specific" (i.e. the number of attachment means (staples) needed to accomplish the surgical procedure for which it is being used). In many surgical procedures, however, the inventors anticipate that the number of attachment means needed will exceed the reasonable capacity of the stapler. In that case the stapler must be withdrawn and additional attachment means cartridges 124 containing additional attachment means 22 can be replaced into the device, until the number of attachment means needed to complete the procedure are disposed in implanted position.

Piston 92 preferably is made of a compressionally molded or sintered graphite, ceramic or thermosetting plastic material. Piston 92 is manufactured to high tolerances, negating the requirement for a sealing detail between piston 92 and stapler barrel 88 wall. Piston 92 is substantially cylindrical in shape. Preferably driver 93 is disposed distally from one surface of piston 92 and is disposed eccentrically from the main piston 92 as shown in FIG. 2. Driver 93 is preferably pie-shaped in cross section, corresponding to the base 73 profile of the staple which it drives.

Attachment means 22 of the present invention can be used to implant the graft in areas where prior methods have failed. While there is usually sufficient healthy tissue at the cephalic end of the aneurysm for attaching the graft, frequently, the caudal end of the aneurysm is broad and distended, as shown in FIGS. 8A, 8B, and 8C, leaving insufficient tissue on which to properly secure the graft. Although the bifurcated graft of FIG. 8B can be used, it would be desirable to implant a graft in the form of FIG. 8C. The present invention enables the implantation of both of the grafts shown in FIGS. 8B, and 8C, where prior methods have failed.

As embodied herein, attachment means 22 are preferably staples, as shown in FIGS. 4A–4G or screws 134 as shown in FIG. 5. Stapler cartridge 124 comprises core 126 in which a plurality of attachment means reservoirs 125 are formed for holding staples 132 or screws 134 until they are implanted. Attachment means 22 are positioned radially about core 126 in reservoirs 125. Core 126 preferably contains spring loaded location device 130 enabling the removal of stapler cartridge 124 from the stapler barrel 88 assembly. Detailing 160 is preferably incorporated within the molding in the form of a flange for indexing the attachment means 22. Detailing 160 preferably facilitates the sequential indexing of the staples 132 into a firing position from which they can be discharged through the aortic graft 10 into the aorta 11 to fix the graft in position.

In patients having calcification of the aorta wall, staple 132 may not penetrate the calcification. If so, staple 132 may not attach into the aorta wall. Nor will the calcification itself provide suitable attachment for the graft. Calcification is typically extremely hard and brittle. Even if penetrated, it will be fragile and provide little opportunity for staple 132 to gain a secure grip. Rather, the object of attachment means is to penetrate calcification and seat in the aorta wall, in either the adventicia or muscularis layers. Thus, it is necessary that the invention be capable of penetrating calcification, if present, in order to provide secure attachment for graft 10.

Where calcification is present, implantation means 80 and attachment means 22 can be modified to penetrate the calcified area of the aorta wall. In an alternative preferred embodiment of the present invention, staple 132 may be replaced with screw 134 as shown in FIG. 5. Piston 92 and driver 93 are adapted to turn the screw 134 head in addition to propelling it into the aorta wall, instead of simply driving in the staple 132 into the aorta wall. This alternative embodiment is particularly useful for driving the attachment means through calcified tissue or where the seating of the attachment means may otherwise be difficult, such as outside the aorta in the common bile duct. Moreover, unlike prior devices in this area, the surgeon can adapt the present invention to these differing circumstances by replacing stapler cartridge 120 of implanting means 80 if necessary, without aborting the repair procedure.

Figure 4E:
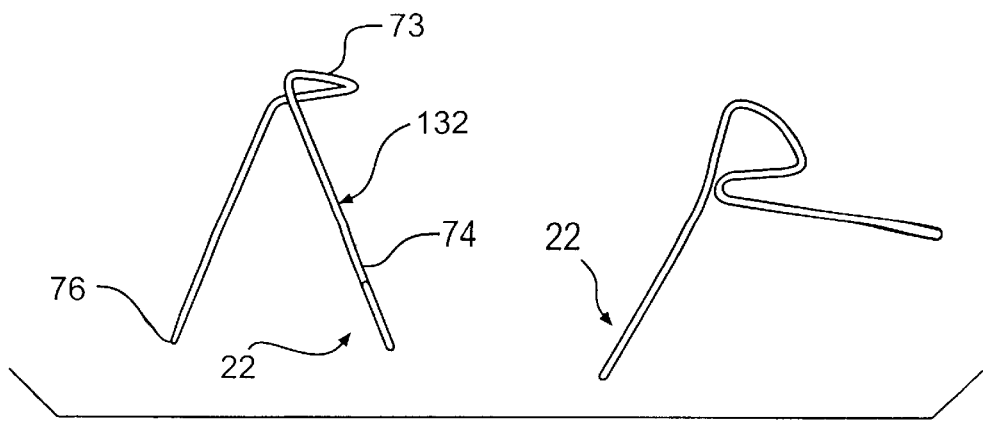
Figure 4F:
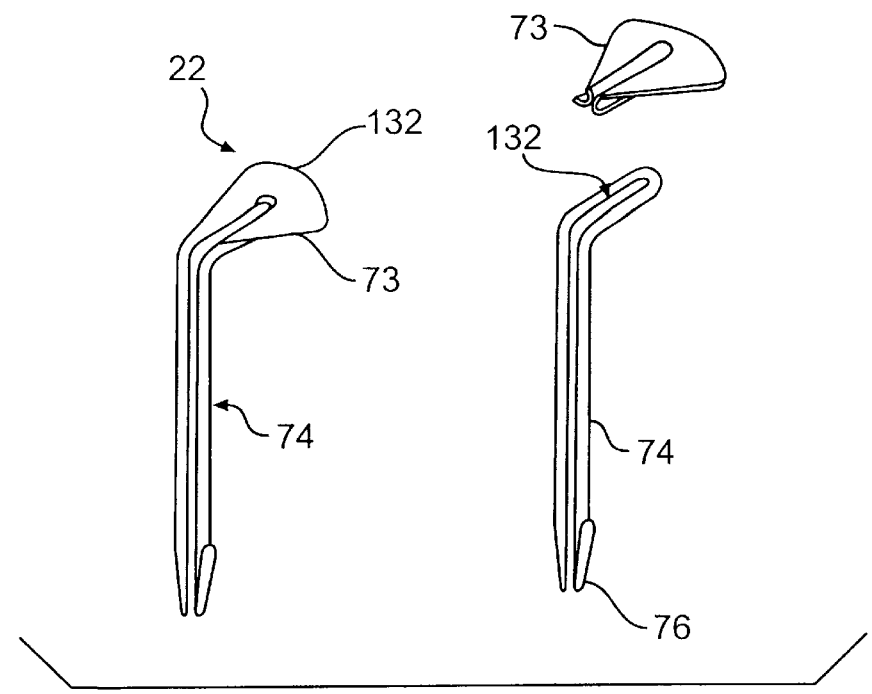
Figure 4G:
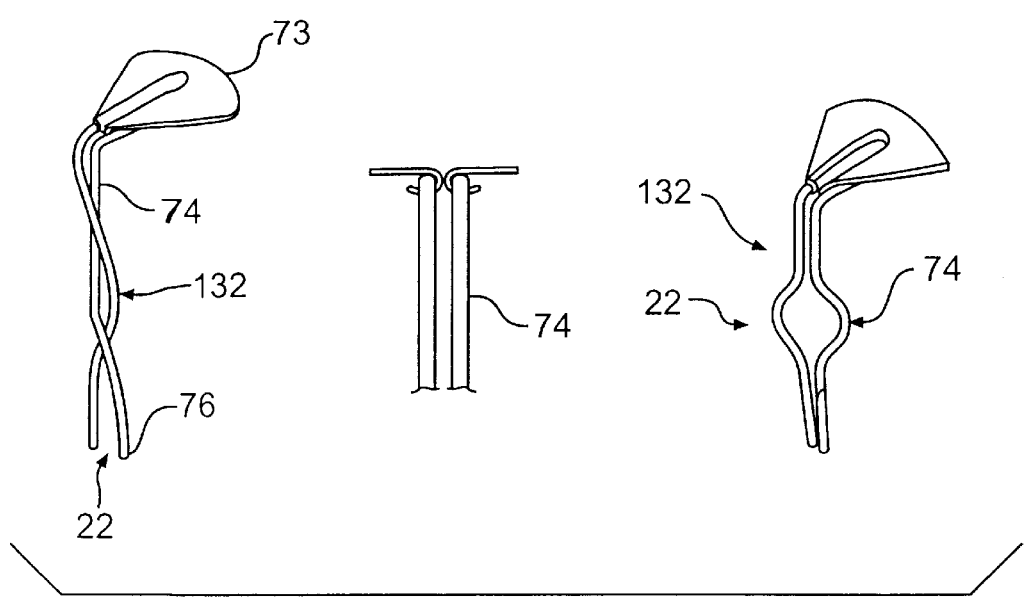

As embodied herein, attachment means 22 can take a variety of forms. For example, various form of attachment means 22 of the present invention are shown in FIGS. 4A–4G and 5. FIG. 4D shows a preferred staple 132 and FIG. 5 shows a preferred screw 134. Various forms of attachment means used in barbs shown in these figures and in Trout '695 could be used. FIGS. 4A, 4B, 4D, 4F, and 4G depict sheet metal staples; FIGS. 4C, 4E, and 4G depict wire staples; FIG. 5 depicts a screw 134, all of which are within the scope of the invention. Additionally, staples could have perforations to aid their assimilation/integration into the surgical site. Preferably, attachment means 22 are formed such that, as they are driven from the staple cartridge 124 by the piston 92, through the aortic graft 10 and into the artery wall, tension in the staple 132 is released and the legs, hooks or barbs shown on staples 132 in FIG. 4, splay out, holding the aortic graft 10 in place.

In the preferred embodiment of the present invention, the staples 132 will be loaded under tension into the staple cartridge 124. Pretensioning the staples 70 will cause them to splay on implantation. For example, the staples 132 shown in FIGS. 4A, 4B, 4C, 4D, 4E, and 4G are adapted to splay upon implantation. Cooperating modifications and variations in implanting means 80 of the invention will be apparent to persons of ordinary skill in order to adapt implanting means 80 to the various attachment means 22 used.

It will be apparent to persons of ordinary skill in the art that variations and modifications can be made to the attachment means 22 of the present invention, in addition to those shown in FIGS. 4 and 5, without departing from the scope and spirit of the invention. For example, an anvil could be used to achieve the desired disposition of the legs of the staples. Nor need the anvil be disposed outside the aorta. Anvils of various types could be incorporated in the implanting device itself, such as at the opening through which the attachment means 22 are ejected to bend the attachment means upon implantation and achieve a secure attachment. Alternatively, the staples 132 can be formed of a "shape memory alloy", such as "Nitinol" wire, so that they resume a preformed position to hold the attachment means in place. Various alternative forms of staple 132, screw 134, or other attachment means 22 could be used, with equally effective results.

For example, in patients having calcification of the aorta, the present invention could be modified to employ a high-speed drilling mechanism, driven off of the piston 92 and driver 94 mechanism disclosed above, with minor modification. Specifically, the mechanism of implanting means 80 would be modified to impart a high speed twisting motion to the attachment means screw 134, as well as driving it through the aorta wall. The screw 134 could be modified to act as both an expendable high-speed drill bit, to penetrate the calcification, and as the attachment means of the present invention once it is pushed through the aperture created in drilling through the calcification. One such modification is shown in FIG. 5.

Further variations in attachment means 22 could be made in conjunction with the shape and design of aortic graft 10, and in its construction. In an alternative to the preferred embodiment, the aortic graft 10 will have a resilient means, such as a round wire in the distal end of the aortic graft 10 to hold the shape of the aortic graft 10 inside the aorta 11 for the attachment means to be better positioned. In another alternative to the preferred embodiment, the aortic graft 10 will have the staples 132 or screws 134 or alternative attachment means 22 built into the end of the aortic graft 10 itself, prepositioned to be driven through the aortic graft 10 and aorta 11. Alternative attachment mechanisms could be achieved by any attachment means that holds the graft in place long enough for the body to establish a firm attachment to the graft. Thus, it is intended that the invention include all of these variations and modifications, provided they come within the scope of the appended claims and their equivalents.

With renewed reference to FIG. 1, as embodied herein, positioning means 96 performs a number of functions simultaneously and comprises a number of unique elements. Positioning tube 100 provides communication between control means 136 and implanting means 80 and disposes implanting means 80 in position to implant attachment means 22. With reference to FIG. 2A, positioning means 96 of the present invention preferably comprises positioning tube 100, having distal positioning tube 97 and proximal positioning tube 106 ends.

Proximal positioning tube 97 preferably further comprises: the proximal end of positioning tube 100, preferably made of thin-walled material, either polymer or stainless steel tube 162; to which an electrodeposited first bellows 108 of copper, silver, or gold-plated material, or other material of comparable integrity and flexibility, is permanently attached; and cuff stabilizer means 98. Proximal positioning tube 97 is that portion of positioning tube 100 that communicates between hand control device 136 and the distal end of positioning tube 100, proximal to the common iliac artery 16 abdominal aorta transition. Distal end of proximal positioning tube 97 ends in first bellows 108 and journal bearing 104.

External surface of proximal positioning tube 97 is coated or sleeved to provide a cuff stabilizer means 98, disposed along the outer circumference of proximal positioning tube 97, at the distal end of proximal positioning tube 97, proximal to first bellows 108. Cuff stabilizer means 98 is preferably an inflatable cuff disposed distal from the surgeon and at the point along positioning means 90 in the iliac artery, proximal to the iliac artery/abdominal artery transition, when implanting device 60 in disposed in the patient to implant the graft 10. Cuff 98 stabilizes implanting device 60 and provides a point of fixture to stabilize the implanting means 80 in operation. Preferably, air is supplied to cuff 98 via a longitudinal indent detail 99 in positioning tube 100 wall that runs along the length of positioning tube 100 to the distal end of proximal positioning tube 97. In an alternative embodiment, inflatable cuff 98 is a component within an introducer tube through which a modified distal positioning tube passes.

Preferably, a first filament 102 of Kevlar is attached to the inside wall of bellows 108 above the corrugations and communicates with hand control device 136. Foreshortening of first filament 102, creates angular movement in bellows 108. Distal end of proximal positioning tube 97 is swaged to journal bearing 104, for attachment to the proximal end of distal positioning tube 106.

Distal positioning tube 106 preferably comprises an electrodeposited second bellows 109 of copper, plated in silver, gold or material of similar integrity and flexibility. Distal positioning tube 106 communicates with and is attached to proximal positioning tube 97 at journal bearing 104, as shown in FIG. 2A. Journal bearing 104 is adapted to allow proximal and distal positioning tubes to communicate that is mounted proximally (the end of distal positioning tube that is nearest the surgeon). Journal 113, is preferably made of stainless steel, is tubular in section, and is permanently attached to the free ends of first and second bellows 108 and 109. Flexible conduit 112, containing an air line, signal and power lines for ultrasound probe 90, guide wire 29, second Kevlar filament 103 or material of similar integrity and flexibility for distal elbow adjustment, and air line for a positioning cuff 98 extending between the hand control device 136 and stapler means 80, passing through the longitudinal axis of the journal 113 while a flexible shaft, 114 emanating in the hand control device 136 of the present invention, is permanently attached into its longitudinal wall. An annular groove 116 about the outer diameter of the journal 113 facilitates the permanent rotational assembly of the distal positioning tube.

Second Kevlar filament 118 is preferably attached to the inside wall of the bellows above the corrugations, distally and communicates with the hand control device 136. As with first bellows, foreshortening the second filament 118 creates angular movement in second bellows 109.

It will be apparent to persons of ordinary skill in the art that various modifications and variation can be made in the positioning means of the present invention without departing from the scope or spirit of the invention, For example, variations in the actuating means of the invention, first and second bellows 108 and 109, and first and second filaments 102 and 118 could be made, or alternative articulation means employed. Additionally, single positioning tube/elbow assembly may work in some instances as opposed to two elbow joints. Thus, it is intended that these variations and modification are included in the invention, provided they come within the scope of the appended claims and their equivalents.

Figure 3:
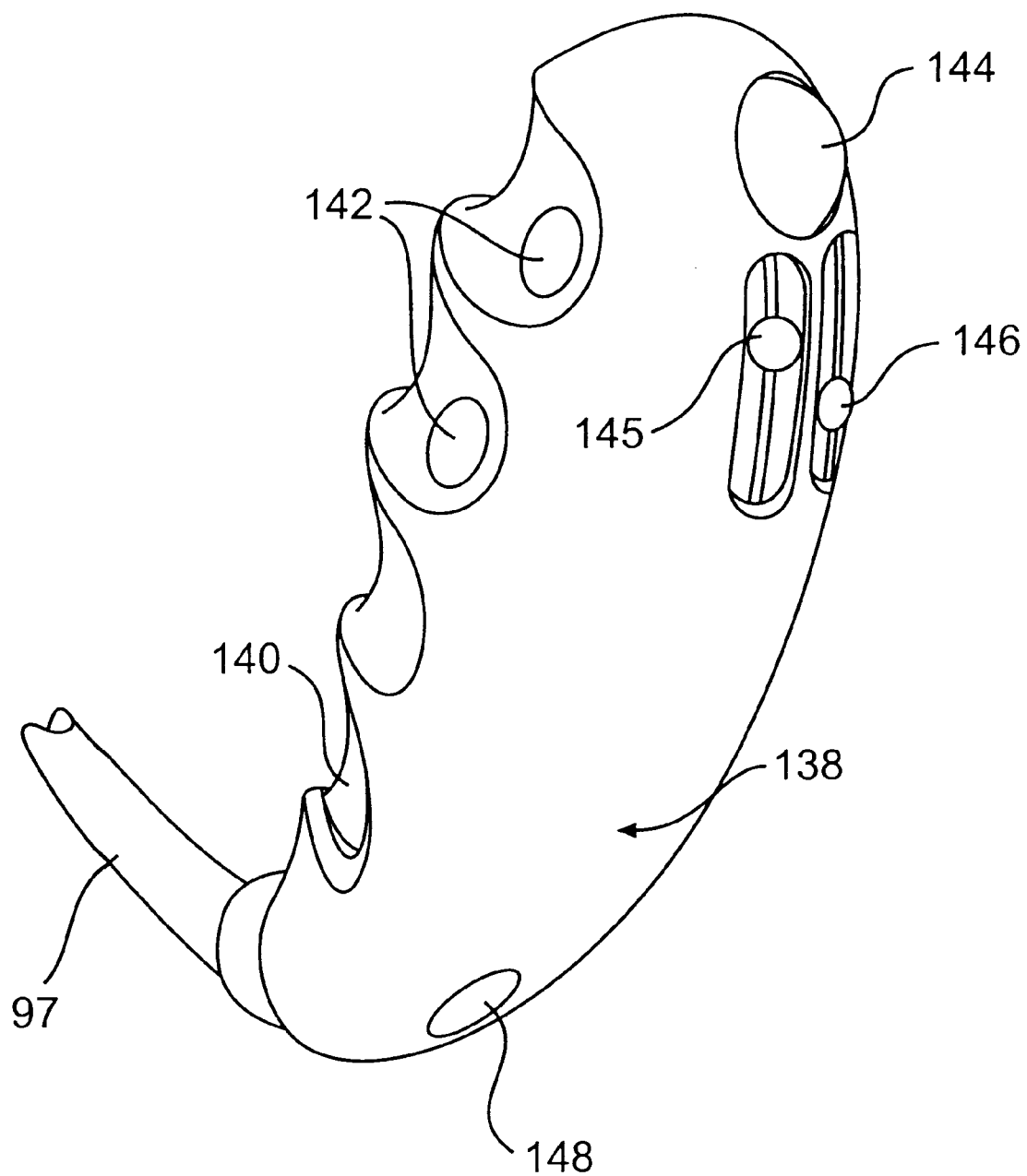
FIG. 3 is an oblique view of the control means and a portion of the positioning means of one embodiment of the present invention.

With reference to FIG. 3, control means 136 of the present invention preferably comprises: a hand grip controller 138, having a trigger 140, air valves 142, thumbwheel 144, first and second slide controls 145 and 146, and injection port 148. Control means 136, controls the function of the stapler 80 and ultrasound probe 90 within the aorta 11. It can be adapted for either right-handed or left-handed use and will provide convenient "one handed" surgery utilizing the present invention. Hand grip controller 138 is set at approximately 90 degrees to the proximal end of proximal positioning tube 97 which enters the hand grip controller 138 parallel to its base, as shown in FIG. 3. The angular relationship between proximal positioning tube 97 and control means 136 is preferably adjustable.

In the preferred embodiment of the invention, hand grip controller 138 is substantially pie-shaped in cross section, the narrowest section corresponding to the location of finger controls; the widest, corresponding to the palm, as shown in FIG. 3. Trigger 140 of hand grip controller 138 is positioned directly above the entry point of proximal positioning tube 97. Trigger 140 preferably controls the flow of compressed air to the stapler 80 barrel tip, which flow is regulated by an associated device to generate the required air pressures and facilitate either single or pulsed air releases through trigger 140 actuation to the stapler 80 barrel tip 122.

In the preferred embodiment of the present invention, air valves 142 are located above the trigger 140 of the hand grip controller 138 of the present invention, for controlling the inflation and deflation of the inflatable cuff 98.

In the preferred embodiment of the present invention, thumbwheel 144 is located at the upper end of the user facing panel, of the hand grip controller 138, for controlling the rotation of stapler 80 and ultrasound probe 90 with respect to the distal positioning tube 97.

Slide controls 146 are preferably located beneath thumbwheel 144, of the hand grip controller 138, for controlling through the foreshortening of the Kevlar filaments 102 to which they are attached, to actuate first and second bellows 108 and 109, which function as elbows within the positioning means 96.

In a preferred embodiment of the present invention, injection port 148 on the hand grip controller 138 is positioned on axis with the distal positioning tube 97. Injection port 148 preferably faces the palm of the user's hand, for providing emergency inflation means for the inflatable cuff 98 of the present invention. This feature provides a fail-safe mechanism for the invention in the event rupture of any of the elements of the invention allows blood to flow through the area of the aneurysm to the iliac artery through which the surgeon is working.

As with each of the other principal elements of the invention, it will be apparent to persons of ordinary skill in the art that various modifications and variation can be made in the control means 136 of the present invention without departing from the scope or spirit of the invention, For example, variations in the types and disposition of controls available to the operator can be made. Controls may be electrical, pneumatic, hydraulic, or of any other appropriate type that can be adapted to use in the invention. It will be apparent to persons of ordinary skill in the art that any appropriate controls that are capable of actuating the invention can be used in lieu of or in addition to those described. Thus, it is intended that these variations and modification are included in the invention, provided they come within the scope of the appended claims and their equivalents.

Implantation of the aortic graft means of the present invention involves several steps.

First, the aortic aneurysm and iliac and femoral vessels must be imaged by one or more of several methods. The procedures discussed in Trout '695 may be used. Alternatively, and preferably, other techniques, such as Computed Tomography (CT), Magnetic resonance (MR), Intravenous Ultrasound (IVUS), arteriography or angiography, ultrasound, or fluoroscopy, could be used to assess the aneurysm and the vessels necessary to gain access to in order to effect a repair. The following parameters are assessed: diameters of the vessels, size and position of necks, lengths, contours, calcification, and abdominal pathology.

Second, a percutaneous needle stick is preferably used to gain access to the femoral or iliac artery. A guide wire is then inserted through the needle into the artery, and advanced into the aorta. The needle is then withdrawn. A catheter is then inserted over the guide wire into the artery, avoiding the need for surgical exposure of the artery.

Third, a small catheter is inserted over the guide wire into the aorta to the position of the aneurysm. The guide wire is removed and an arteriogram is obtained. This is done be injecting radiopaque contrast material through the catheter to visualize the lumen of the aorta, iliac and femoral vessels. Alternatively, an intravenous ultrasound probe could be used to visualize the vessels, avoiding the need for an arteriogram.

Figure 9A:
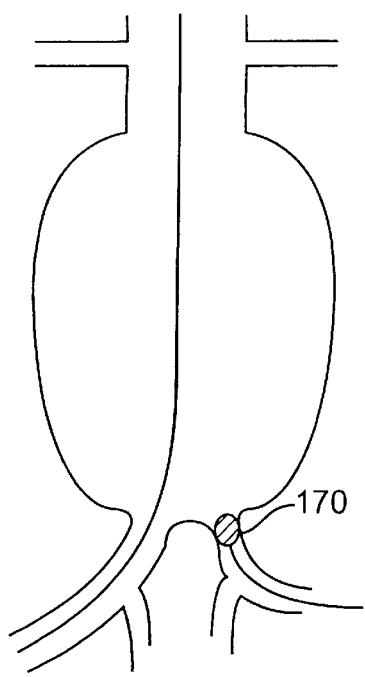
FIG. 9A is a coronal view of the aneurysm, in which a occlusal balloon has been inserted in one of the iliac arteries and a guide wire has been inserted in the other iliac artery, extending into the aneurysm and beyond its cephalic end.
Figure 9B:
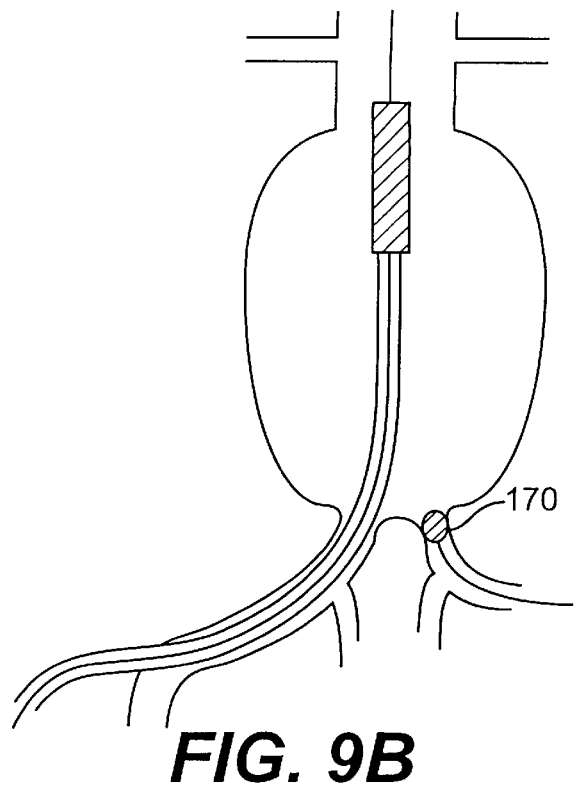
FIG. 9B is a coronal view of the aneurysm, in which a graft and catheter system has been inserted along the guide wire of FIG. 9A.
Figure 9C:
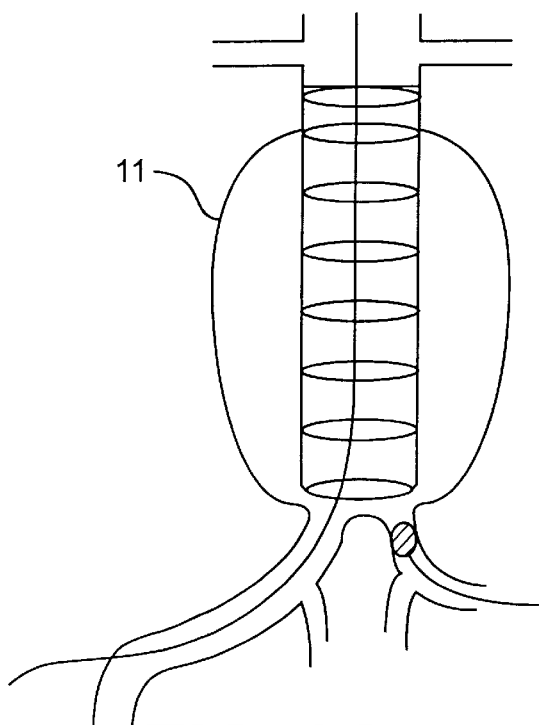
FIG. 9C is a coronal view of the aneurysm, in which a graft and catheter system has been implanted at the cephalic end of the aneurysm and in which insufficient neck exists at the caudal end of the aortic aneurysm proximate the iliac arteries for attachment of the caudal end of the graft by prior methods.
Figure 9D:
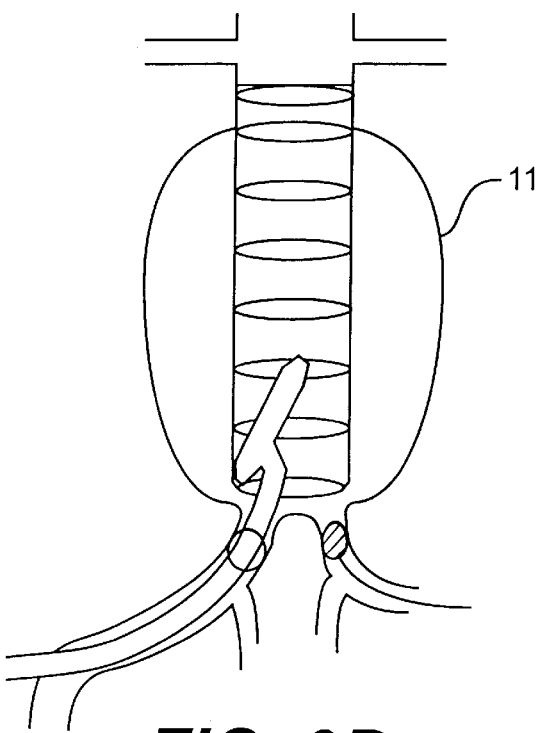
FIG. 9D is a coronal view of the aneurysm, in which a graft has been implanted at the cephalic end of the aneurysm and into which the distal end of the positioning means, the attachment means, and the implantation means of a preferred embodiment of the present invention has been disposed.
Figure 10A:
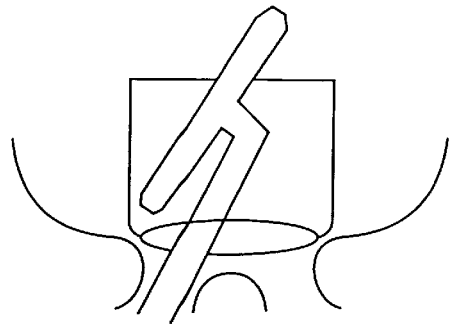
FIG. 10A is a coronal view of the implantation means of the present invention disposed to implant the attachment means of the present invention.
Figure 10B:
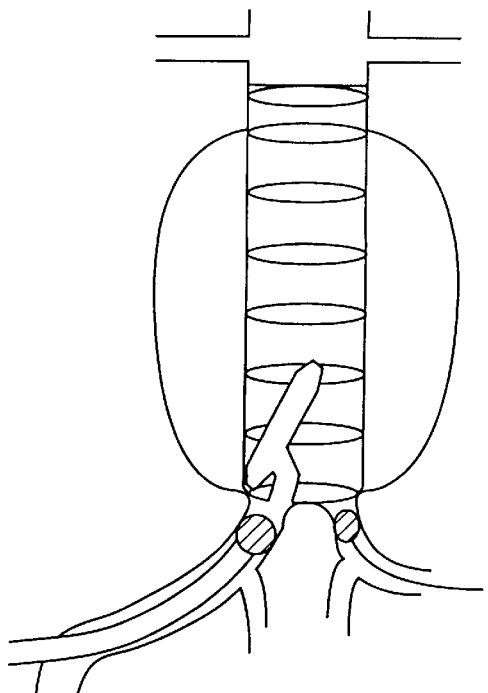
FIG. 10B is a coronal view of the implantation means of the present invention implanting the attachment means of the present invention.
Figure 10C:
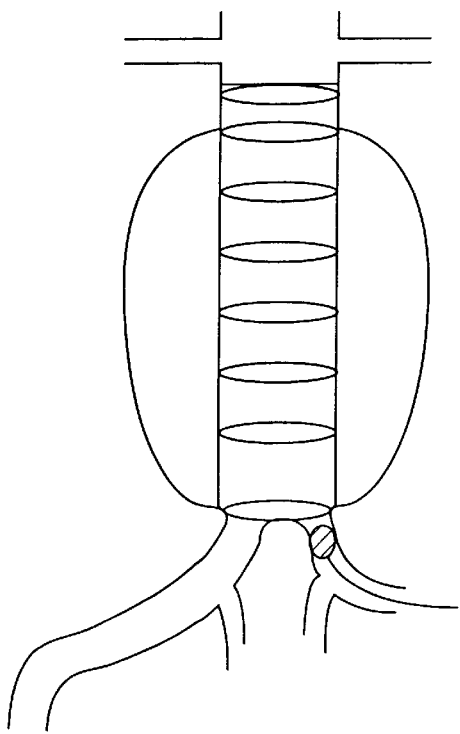
FIG. 10C is a coronal view of the graft, implanted in the aortic aneurysm, after the implanting device of the present invention and guide wire have been removed.
Figure 10D:
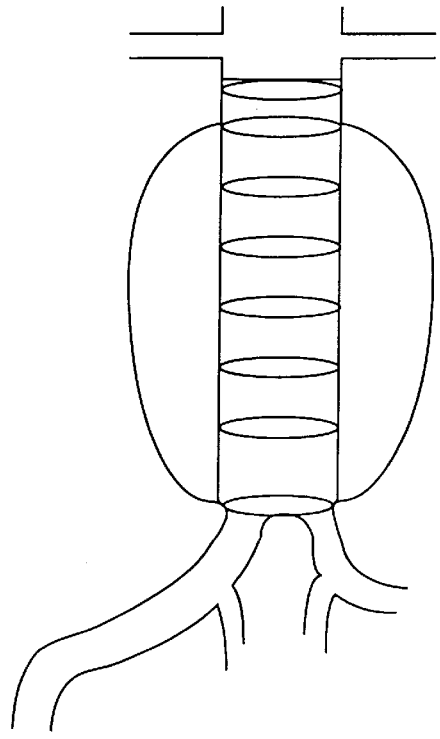
FIG. 10D is a coronal view of the graft, after the implantation device of the present invention, guide wire, and occlusal balloon have been removed.

Fourth, a needle stick is done on the contralateral femoral artery and a guide wire is placed in the contralateral femoral artery. The guide wire is passed to the level of the contralateral common iliac artery. An occlusion balloon is passed over the guide wire and inflated to occlude the common iliac artery at its origin, as shown in FIG. 9A.

Fifth, a guide wire is reinserted through the catheter on the ipsilateral femoral artery after the angiogram is obtained or the vessels are measured using ultrasound. Progressively larger catheters are then inserted until passage of a catheter of sufficient size to allow passage of the graft and necessary attachment instruments is achieved. This last catheter (also known as a "sheath") will be placed in the abdominal aorta or in the common iliac artery depending upon the portion of the procedure is being performed. The distal end of the sheath is maintained below the caudal level of the graft.

If necessary, this dilatation can be facilitated by either balloon dilatation or atherectomy catheter. Alternatively, an incision is made in the femoral artery 17 or iliac artery 16 to provide a means of access to aneurysm 12. At this point the guide wire is in place and the vessels have been enlarged to permit passage of the attachment instruments and graft.

Sixth, a graft package is assembled and compressed, comprising a balloon catheter, stent, and aortic graft. The package is inserted over the guide wire and through the sheath. The package is then passed to the position of the cephalic aortic neck, just below the renal arteries and just above the level where the aorta dilates into the aneurysm, at a position caudal to the renal arteries and cephalad to the dilatation of the aorta.

Seventh, the cephalic end of the graft is implanted. The balloon is distended, which causes the stent to expand and the graft to contact the aortic neck. The graft held in place at the cephalic end by friction between the stent, graft and aortic wall. Alternatively, it can be held in place by hooks, or by staples. Alternatively, the graft can be implanted by the procedures and device disclosed in the Trout '695 patent.

Eighth, the balloon catheter used to implant the cephalic end of the graft is removed.

Ninth, the implantation device 60 of the present invention is inserted over the guide wire through the sheath to the level of the common iliac artery on the ipsilateral side. Alternatively, the device may be inserted without using a guide wire, if the guide wire would limit mobility of the implanting means 80.

Tenth, the cuff is disposed at the level of the common iliac artery at the ipsilateral side and inflated to stabilize the implantation device 60 and, in particular, implantation means 80.

Eleventh, the implantation means—stapler 80 is maneuvered into position at the caudal end of the graft, adjacent the chamfered portion of the graft.

Twelfth, attachment means 22 are implanted circumferentially around the caudal end of the graft until no leaks are detected. This is verified by various imaging techniques (IVUS, arteriography, ultrasound, or spiral CT).

Thirteenth, the stapler device is then removed.

Fourteenth, the aorta is flushed to the outside through the sheath, so that any loose material that may have been created by manipulation of the graft or implanting device is flushed to the outside of the body rather than allowed to embolize into the arteries of the leg or pelvis.

Fifteenth, the Contralateral occlusion balloon is then deflated and removed.

Sixteenth, the sheath is removed.

Finally, the artery is compressed until bleeding ceases. On occasion, the hole in the artery will not self-seal and will require direct surgical repair.

It will be apparent to persons of ordinary skill in the art that various modifications and variations can be made in the above procedure, without departing from the spirit of the invention. For example, the steps of imaging and assessing the aorta and iliac and femoral arteries can be accomplished in various ways that are well known in the art. The use of a sheath is not necessary. The graft could be enclosed in various ways that would be apparent to those of ordinary skill in the art that would eliminate the need for the sheath. Further the method of attachment of the cephalic end of the graft is not necessarily limited to any of the above methods, provided a secure, leak-proof attachment is achieved. Other variations or modifications of the process will be apparent to persons of ordinary skill in the art. Thus, it is intended that the invention include these variations, provided they come within the scope of the appended claims and their equivalents.

We claim:

1. A device having a distal end for temporary introduction into an animal for attaching a repair member to an animal vessel, and a proximal end interconnected to said distal end for use external of the animal, said device comprising:

means for storing plural attachment members for attaching the repair member to the vessel wherein said means for storing plural attachment members being located at said distal end of said device; and means for inserting one of said attachment members at a time through the repair member and the vessel to thereby connect the repair member and the vessel, wherein said means for inserting being located at said distal end of said device;

means for controlling the operation of said means for storing and means for inserting such that said means for storing delivers one attachment member at a time to said means for inserting and said means for inserting applies pressure to said attachment member to insert the attachment member through the repair member and the vessel, wherein said means for controlling being located at said proximate end.

2. The device of claim 1 wherein said repair member comprises a surgical graft.

3. The device of claim 1 wherein said means for storing comprises a multi-chambered cylinder, wherein one attachment member is stored in each chamber.

4. The device of claim 3 wherein said distal end comprises a cylinder and said means for storing is co-axial with and rotatable within said distal end.

5. The device of claim 4 wherein the rotation of said means for storing aligns a chamber therein with the means for inserting such that an attachment member may be delivered from said chamber to the means for inserting.

6. The device of claim 3 wherein said means for storing is removably attached to said distal end such that said storing means is removable to thereby permit reloading the distal end of the device with attachment members.

7. The device of claim 1 wherein an attachment member comprises a staple having a head connecting first and second prongs, wherein said prongs are compressed together while the staple is in the means for storing and wherein the ends of the prongs distal from said head separate from each other after the prongs are inserted through the repair member and the vessel.

8. The device of claim 7 wherein the staple prongs are comprised of wire.

9. The device of claim 7 wherein the staple prongs are comprised of flat strip material.

10. The device of claim 7 further comprising at least one barb extending from the staple prongs.

11. The device of claim 7 wherein the staple prongs are twisted around each other.

12. The device of claim 1 wherein an attachment member comprises a means for drilling through a hardened vessel.

13. The device of claim 1 wherein an attachment member comprises a screw and the means for inserting comprises means for rotationally driving a screw through the repair member and the vessel.

14. The device of claim 13 further comprising at least one barb extending from the screw.

15. The device of claim 1 further comprising means connected to said distal end for delivering pressurized air from said proximate end of said device to the means for inserting to power said inserting means.

16. The device of claim 15 further comprising means connected to said distal end for delivering pressurized air from said proximate end of said device to the means for storing to power said storing means.

17. The device of claim 1 further comprising means connected to said distal end for delivering electricity from said proximate end of said device to the means for inserting to power said inserting means.

18. The device of claim 1 further comprising an elongated catheter connecting the proximal and distal ends of the device and wherein said distal end is selectively orientable relative to said catheter.

19. The device of claim 18 wherein the distal end is rotatable and angularly pivotable relative to said catheter.

20. The device of claim 18 further comprising an inflatable sleeve for maintaining the position of said catheter within the animal vessel wherein said inflatable sleeve being located on said catheter adjacent said distal end.

21. The device of claim 1 further comprising means for providing a visual representation of the vessel surrounding the distal end of the device, said means being located adjacent said distal end.

22. The device of claim 1 further comprising ultrasound means for determining the condition of the vessel, said ultrasound means being located adjacent said distal end.

23. A device having a distal end for temporary introduction into an animal for attaching a surgical graft to an animal blood vessel, and a proximal end interconnected to said distal end for use external of the animal, said device comprising:

a multi-chambered cylinder, co-axial and rotatable within the distal end, for storing an attachment member in each chamber, said cylinder being located at said distal end;

at least one attachment member to attach the surgical graft to the vessel;

means for inserting attachment members through the surgical graft and into the vessel to thereby connect the graft and the vessel, said inserting means being located at said distal end, said multi-chambered cylinder supplying said inserting means with attachment members;

means located at said distal end for providing a visual representation of the vessel surrounding the distal end of the device;

means located at said proximate end for (i) controlling the rotation of said multi-chambered cylinder so that each chamber thereof may be aligned in turn with the means for inserting to provide an attachment member to the means for inserting and for (ii) controlling the insertion of an attachment member by the means for inserting through the graft and into the vessel; and an elongated catheter connecting the proximal and distal ends and providing means for delivering electricity and pressurized air between said proximal and distal ends.

24. A method of implanting a repair member in a vessel, using an implantation device comprising positioning means, means for storing plural attachment means, implanting means for implanting said attachment means to implant the repair member in the vessel, and control means for controlling the operation of said implantation device, wherein said implantation device has a distal end and said means for storing being located in said distal end, said method comprising the steps of:

gaining access to the vessel, sufficient to allow passage of the repair member and at least the distal end of the implantation device into the vessel to a point of repair;

assessing the parameters of the vessel being repaired and selecting an appropriate repair member for the vessel;

passing the repair member and at least the distal end of the implantation device into the vessel to a level at which the repair is to be effected;

implanting a distal end of the repair member in the vessel;

stabilizing the implantation device in the vessel being repaired;

maneuvering the implantation device at a caudel end of the repair member;

actuating the implanting means to implant the attachment means from the storing means circumferentially around the caudel end of the repair member without removing the implantation device from the vessel, until no leaks are detected;

removing the implantation device; and sealing access to the vessel.

25. The method of claim 24, wherein said attachment means comprises a surgical staple.

26. The method of claim 24, wherein said vessel is an aneurysm that is calcified and wherein said attachment means comprises a screw adapted to penetrate calcified areas of the aorta.

27. The methods of claim 24, wherein said method further comprises the step of using visualization means positioned within the distal end of the implantation device to determine the position of the implantation means.

28. The methods of claim 24, wherein said method further comprises the step of using ultrasound means positioned within the distal end of the implantation device for determining the condition and status of the vessel.

* * * * *